(12) United States Patent
Hettrick et al.

(10) Patent No.: US 7,676,268 B2
(45) Date of Patent: Mar. 9, 2010

(54) MEDICAL METHODS AND SYSTEMS INCORPORATING WIRELESS MONITORING

(75) Inventors: Douglas A. Hettrick, Andover, MN (US); Kenneth C. Gardeski, Plymouth, MN (US); H. Toby Markowitz, Roseville, MN (US); Sameh Sowelam, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 437 days.

(21) Appl. No.: 11/565,283

(22) Filed: Nov. 30, 2006

(65) Prior Publication Data

US 2008/0132800 A1 Jun. 5, 2008

(51) Int. Cl.
*A61N 1/00* (2006.01)
(52) U.S. Cl. .............................. 607/32; 607/17; 600/513
(58) Field of Classification Search ................ 607/1–28, 607/32; 600/300–595
See application file for complete search history.

(56) References Cited

U.S. PATENT DOCUMENTS

| | | | |
|---|---|---|---|
| 5,423,883 A | 6/1995 | Helland | |
| 5,549,650 A | 8/1996 | Bornzin et al. | |
| 5,549,652 A | 8/1996 | McClure et al. | |
| 5,628,777 A | 5/1997 | Moberg et al. | |
| 5,738,096 A | 4/1998 | Ben-Haim | |
| 6,002,963 A | 12/1999 | Mouchawar et al. | |
| 6,009,349 A | 12/1999 | Mouchawar et al. | |
| 6,261,247 B1 | 7/2001 | Ishikawa et al. | |
| 6,285,898 B1 | 9/2001 | Ben-Haim | |
| 6,360,123 B1 | 3/2002 | Kimchi et al. | |
| 6,363,940 B1 | 4/2002 | Krag | |
| 6,592,518 B2 | 7/2003 | Denker et al. | |
| 6,675,810 B2 | 1/2004 | Krag | |
| 6,698,433 B2 | 3/2004 | Krag | |
| 6,812,842 B2 | 11/2004 | Dimmer | |
| 6,822,570 B2 | 11/2004 | Dimmer et al. | |
| 6,889,833 B2 | 5/2005 | Seiler et al. | |
| 6,918,919 B2 | 7/2005 | Krag | |

(Continued)

FOREIGN PATENT DOCUMENTS

EP 1252860 A 10/2002

(Continued)

OTHER PUBLICATIONS

Solomon SB, et al. Contraction-relaxation coupling: determination of the onset of diastole. Am J Physiol. Jul. 1999;277(1 Pt 2):H23-7.

(Continued)

*Primary Examiner*—Scott M Getzow
(74) *Attorney, Agent, or Firm*—Michael C. Soldner; Michael J. Ostrom; Stephen W. Bauer

(57) ABSTRACT

Medical systems and methods incorporate monitoring of at least two implanted markers, each of which is adapted to wirelessly transmit a signal in response to a wirelessly transmitted excitation signal; the response signals are converted into positional information for the two markers. The systems and methods further incorporate both, or one of, an implanted sensing member and/or an implanted therapy delivery device. Signals received from the sensing member may be collated with the positional information. A therapy delivered from the therapy delivery device may be adjusted according to the positional information.

12 Claims, 17 Drawing Sheets

U.S. PATENT DOCUMENTS

| | | | |
|---|---|---|---|
| 7,043,292 | B2 | 5/2006 | Tarjan et al. |
| 2003/0120150 | A1 | 6/2003 | Govari |
| 2003/0204209 | A1 | 10/2003 | Burnes et al. |
| 2004/0106871 | A1 | 6/2004 | Hunyor et al. |
| 2004/0138554 | A1* | 7/2004 | Dimmer et al. ............. 600/423 |
| 2004/0172079 | A1* | 9/2004 | Chinchoy .................... 607/17 |
| 2005/0099290 | A1 | 5/2005 | Govari |

FOREIGN PATENT DOCUMENTS

| | | |
|---|---|---|
| EP | 1447681 A | 8/2004 |
| EP | 1552795 A | 7/2005 |
| WO | 2005067563 A2 | 7/2005 |
| WO | WO2005067792 A | 7/2005 |

OTHER PUBLICATIONS

International Search Report, PCT/US2007/085761, Nov. 27, 2008, 9 pages.

* cited by examiner

MEDICAL METHODS AND SYSTEMS INCORPORATING WIRELESS MONITORING

TECHNICAL FIELD

The present invention relates to medical systems including wireless monitoring, and more particularly, to the use of wireless monitoring in conjunction with implanted medical devices.

BACKGROUND

Wireless monitoring systems including biocompatible markers for bodily implantation are commercially available. One such system includes leadless AC electromagnetic markers or transponders. Coupled with a localization system, the transponders send signals which can be used to generate objective location instructions to guide delivery of therapy, for example, radiation therapy. In addition to applications such as this one, wherein the markers are used to mark specific locations in a body to facilitate the targeting of therapy delivery, such leadless markers have been described for use in tracking activity/motion of various body parts. However, there is a need for new systems and methods employing wireless monitoring to generate positional information facilitating medical diagnoses and/or therapy delivery.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
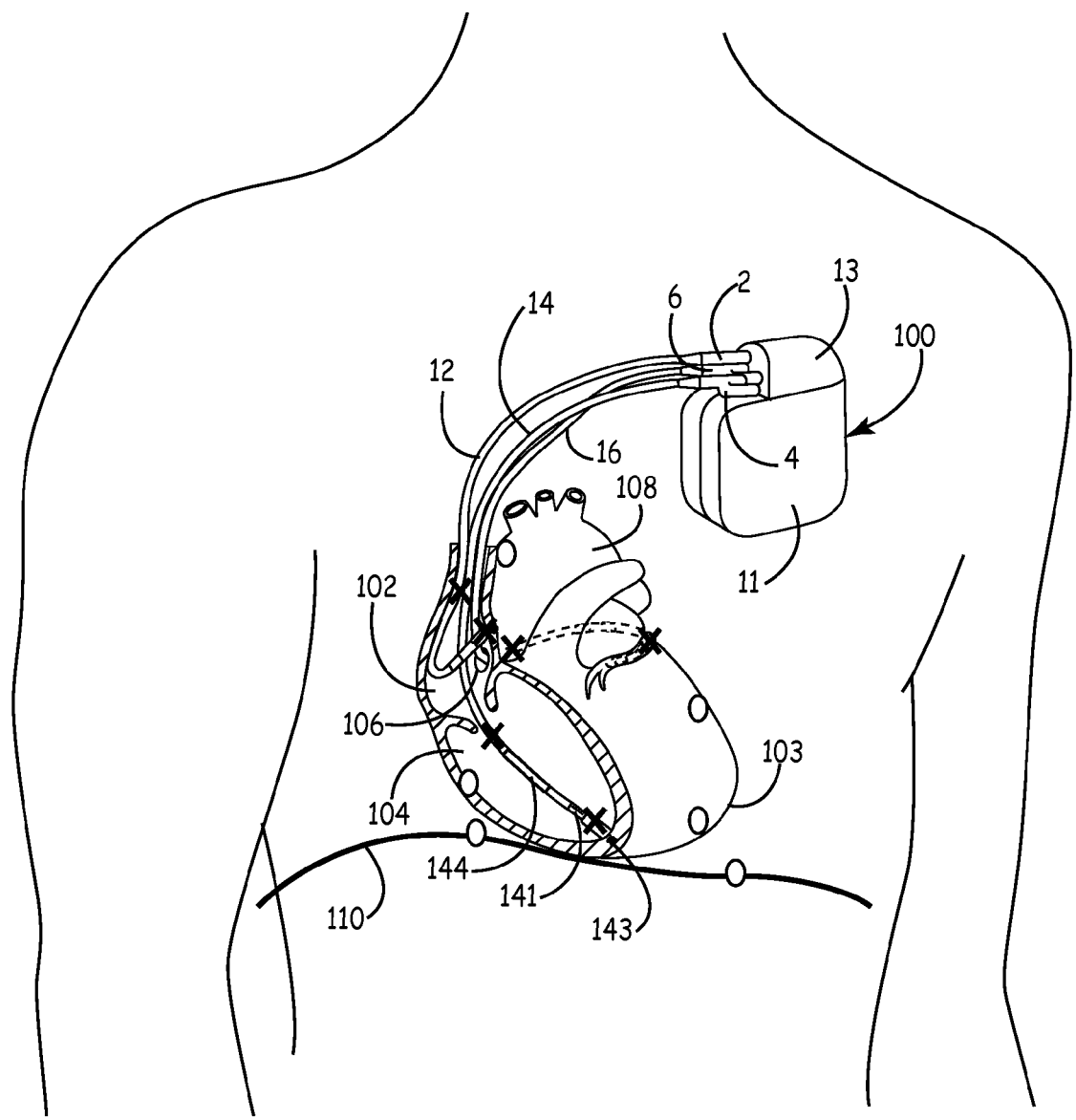
FIG. 1 is a schematic depiction of implanted portions of a system, according to some embodiments of the present invention.

FIG. 1 is a schematic depiction of portions of a system implanted in a patient, according to an embodiment of the present invention; exemplary external components of the system are shown in FIG. 4 and will be described below in conjunction with FIG. 4. FIG. 1 illustrates an implantable medical device (IMD) 100 implanted in a pectoral region of the patient and including a housing or can 11, which encloses a power supply and electronic circuitry of IMD 100, and a device header 13, which includes device contacts coupled by wire feedthroughs to the electronics enclosed in can 11. Lead bodies 12, 14 and 16, which are coupled to IMD100 via electrical connector terminals 2, 4, and 6, respectively, plugged into header 13, are shown implanted in a right atrium (RA) 102, a right ventricle (RV) 104 and a coronary sinus (CS) 106. According to the illustrated embodiment, lead body 14 includes a tip electrode 143, a proximal ring electrode 141 and a more proximal pressure transducer 144, all coupled thereto, wherein each electrode 141, 143 and transducer 144 may be coupled to electronic circuitry of IMD 100 via a corresponding lead extending within lead body 14 and being terminated in a corresponding lead connector contact (not shown), of connector terminal 4, each of which connector contacts are coupled to a corresponding device contact in header 13. Electrodes 141 and 143, for example formed from a platinum/iridium alloy, may function as either or both a sensing member and/or a therapy delivery member for the illustrated system, and transducer 144 forms a sensing member for the system. Lead body 14 may include one or more additional therapy delivery members, examples of which include, without limitation, a lumen and port for drug delivery and one or more defibrillation electrodes; and, although not shown, it should be understood that each of lead bodies 12 and 16 include one or more sensing and/or therapy delivery members. Appropriate materials and construction methods for lead bodies 12, 14, 16, as well as connector terminals 2, 4, 6 thereof, are well known to those skilled in the art of lead construction.

FIG. 1 further illustrates the system including wireless transponder-type markers indicated with X's and O's at various locations which may be selected for wireless positional monitoring. Markers X are tethered markers, that is, markers X may be coupled to a lead body, for example, any or all of lead bodies 12, 14 and 16, or to any other interventional elongate member, for example, a guide wire or catheter; it should be noted that the scope of the present invention is not limited by any of the illustrated locations of markers X, each location merely being illustrative of a feasible location coinciding with a feasible positioning of each lead 12, 14, and 16 associated with some embodiments of the present invention. Each of markers O is independently implantable of one another, and other implanted components; markers O are shown implanted on, or in, a wall of RV 104, a wall of left ventricle (LV) 103, a wall of an aorta 108, and a diaphragm 110. Again, it should be noted that the scope of the present invention is not limited to any of the illustrated locations of markers O, each location just being illustrative of a feasible location associated with some embodiments of the present invention. Embodiments of the present invention may include one or more markers X without any independent markers O, or visa versa, or a combination of the two types of markers. An example of one of markers X is described in greater detail in conjunction with FIG. 2, and two examples of independent markers O are described in conjunction with FIGS. 3A-D.

According to embodiments of the present invention, markers X and O are passive assemblies that can be excited to generate a signal in response to an excitation signal wirelessly transmitted from outside the body of the patient. Markers X and O are preferably formed as inductor-capacitor (LC) resonant circuits, for example, that include a coil wound about a ferromagnetic core and a capacitor coupled to the coil. When excited from a distant source at a resonant frequency for markers X, O, the markers will store energy at the resonant frequency. When the external excitation is removed, the stored energy will be radiated by the inductor of each marker X, O in the form of electromagnetic energy that can be detected by a sensor array coupled to a marker signal processor outside the body of the patient. The excitation signal source, sensor array and marker signal processor will be defined in greater detail in conjunction with FIG. 4. According to an exemplary embodiment, a diameter of markers X, O is approximately 2 mm and a length of markers X, O is approximately 5 mm. Certain embodiments of markers X, O are constructed according to the teachings of U.S. Pat. No. 6,889,833 in columns 5-7 thereof, related to FIGS. 4A-B thereof, which incorporated herein by reference in it's entirety.

Figure 2:
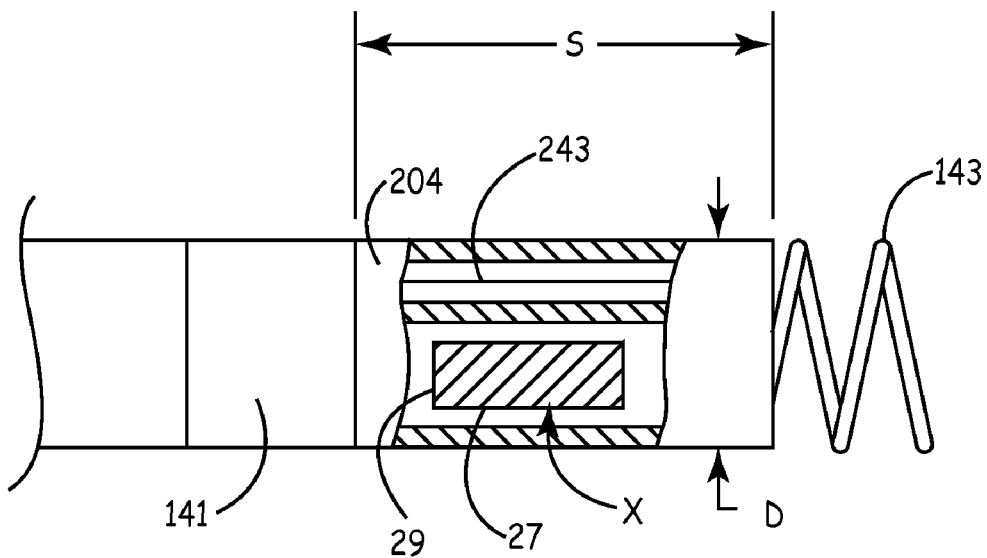
FIG. 2 is a plan view, including a cut-away section, of a distal portion of an implantable lead body, according to some embodiments of the present invention.

FIG. 2 is a plan view, including a cut-away section, of a distal portion of lead body 14, according to some embodiments of the present invention. FIG. 2 illustrates marker X encased within an insulative portion 204 of body 14, being disposed between electrodes 141 and 143 and alongside a lead 243, which extends proximally within body 14 to coupled electrode 143 to IMD 100. According to the illustrated embodiment, insulative portion 204, for example, molded from a polyurethane having a hardness of approximately 75 D, further extends between marker X and lead 243, for example, to maintain a stable position of the marker within lead body 14 and to electrically isolate lead 243 from marker X.

FIG. 2 further illustrates marker X including a conductor 27, for example, 45-52 gauge wire, wound, for example, in 800-2000 turns, about a ferromagnetic core 29, for example, a ferrite rod having a diameter between approximately 0.2 mm and approximately 0.7 mm, and a length between approximately 2 mm and approximately 12 mm. According to preferred embodiments, marker X further includes a capacitor (not shown) electrically connected in parallel to coil 27. According to an exemplary embodiment, an outer diameter D of insulative portion 204 ranges from approximately 1.5 mm to approximately 1.8 mm and a spacing S between electrode 143 and electrode 141 ranges between approximately 10 mm and approximately 12 mm. Given these dimensions for portion 204, those skilled in the art of lead construction will appreciate, that marker X having a length between approximately 2 and 10 mm and a diameter between approximately 0.6 mm and 1 mm should fit, along with lead 243, within insulative portion 204.

With reference back to FIG. 1, it may be appreciated that electrode 143 fixed in an apical portion of RV 104 maintains a position for the marker X of FIG. 2, with respect to the apex, and another marker X of lead body 14, which is shown positioned in proximity to a tricuspid valve between RA 102 and RV 104. Excitation and collection of responses from the two markers X of implanted lead body 14 provides positional information over time. Such positional information can be used to track a changing dimension of RV 104, both over a short term, for example, over a cardiac cycle or a successive series of cardiac cycles, and over a long term, for example, over a series of interrogations spaced apart in time at specific points in the cardiac cycle. In one example, an end diastolic dimension would be proportionate to myocardial stretch, or length, as well as chamber volume. End diastolic ventricular volume is a generally accepted index of ventricular pre-load, which, in turn, is a widely recognized determinant of cardiac performance. Positional information gleaned from markers X of lead body 14 may be combined with positional information gleaned from any other implanted markers X, for example, coupled to lead body 12 and/or lead body 16, and/or from any of implanted independent markers O. Specific examples of marker placement, for particular diagnostic evaluations, will be described in greater detail below, in particular, in conjunction with FIGS. 7A-B, 8A-B and 9A-B.

According to some embodiments of the present invention, markers X, O can be interrogated during an implant procedure in order to evaluate hemodynamic response, for example, via changes in ventricular dimension, to pacing stimulation at alternate pacing sites for any or all of lead bodies 12, 14, 16. This feedback may facilitate the positioning of pacing electrodes, coupled to the lead bodies, for site-specific pacing, wherein pacing stimulation is targeted to a site where the pacing can most closely match natural/physiological conduction. Markers X may also be interrogated during the implant procedure to collect positional information that can aid in the navigation of any or all of leads 12, 14, 16 to a particular site.

Figure 3A:
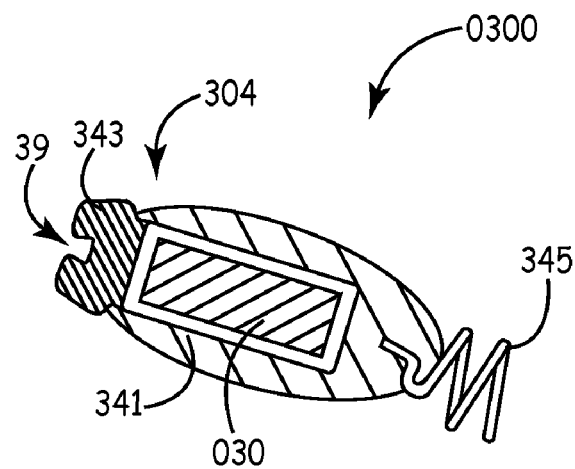
FIG. 3A is plan view, including a cut-away section, of an implantable marker, according to some embodiments of the present invention.
Figure 3B:
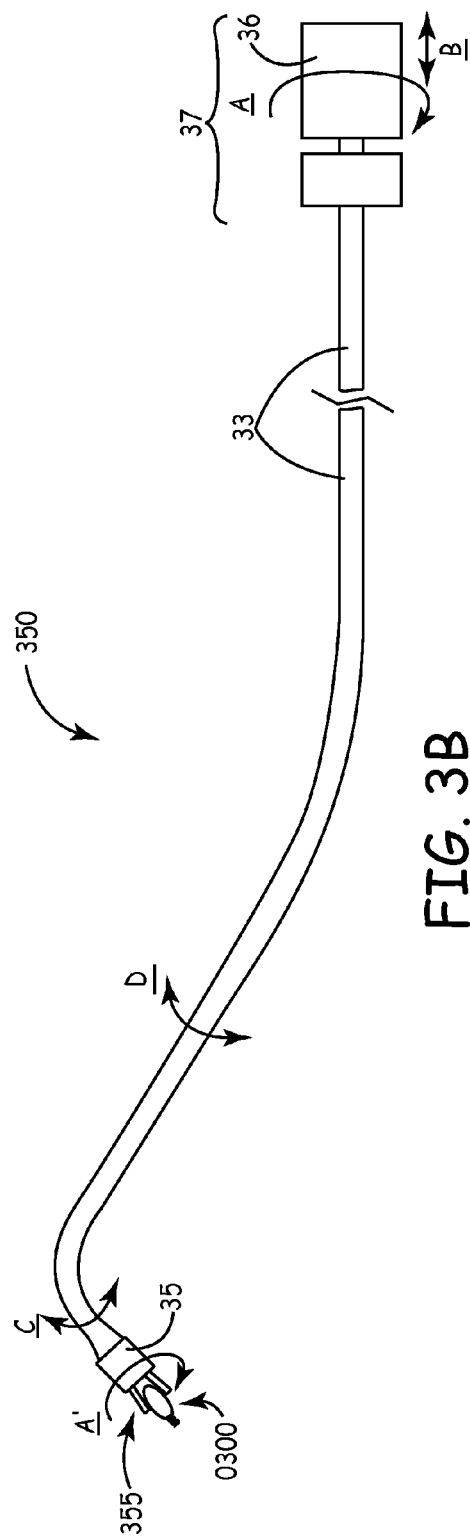
FIG. 3B is a plan view of a delivery tool adapted to implant a marker, according to some embodiments of the present invention.

FIG. 3A is plan view, including a cross-section, of an implantable independent marker assembly O300, according to an embodiment of the present invention; and FIG. 3B is a plan view of a delivery tool 350 which may implant marker assembly O300, according to some embodiments of the present invention. FIG. 3A illustrates marker assembly O300 including a marker O30 contained within a body 304 to which a fixation helix 345 is coupled. According to some embodiments, marker O30 includes the same components as previously described for marker X and is sized such that body 304 has a maximum outer diameter between approximately 1 mm and approximately 3 mm and a length between approximately 4 mm and approximately 6 mm. Examples of suitable materials for body 304 include, without limitation, polymer, for example, polyurethane (PU) or polyetheretherketone (PEEK), glass and ceramic.

According to the illustrated embodiment, body 304 includes a main portion 341 forming a receptacle to hold marker O30 and a cap 343 closing off main portion 341 to contain marker O30; if cap 343 and portion 341 are formed of PU, cap 343 may be bonded to portion 341 with a PU adhesive, or if cap 343 and portion 341 are formed of PEEK, cap 343 may be ultrasonically welded to portion 341. According to alternate embodiments, body 304 as a whole is formed around marker O31, for example molded or cast, to embed the marker therein. FIG. 3B illustrates tool 350 including a handle 37 coupled to a proximal end of a shaft 33, and grippers 355, which extend from a distal end of shaft 33, holding marker assembly O300 for implantation. FIG. 3B further illustrates handle 37 including a portion 36 which may be rotated, per arrow A, to rotate grippers, per arrow A', in order to engage fixation helix 345 in tissue, for example, myocardium; portion 36 of handle 37 may also be moved longitudinally, per arrow B, in order to open and close grippers 355 by pushing and pulling grippers 355 out from and into, per arrow B', a distal head 35 of shaft 33, as is illustrated in FIG. 3C.

Figure 3C:
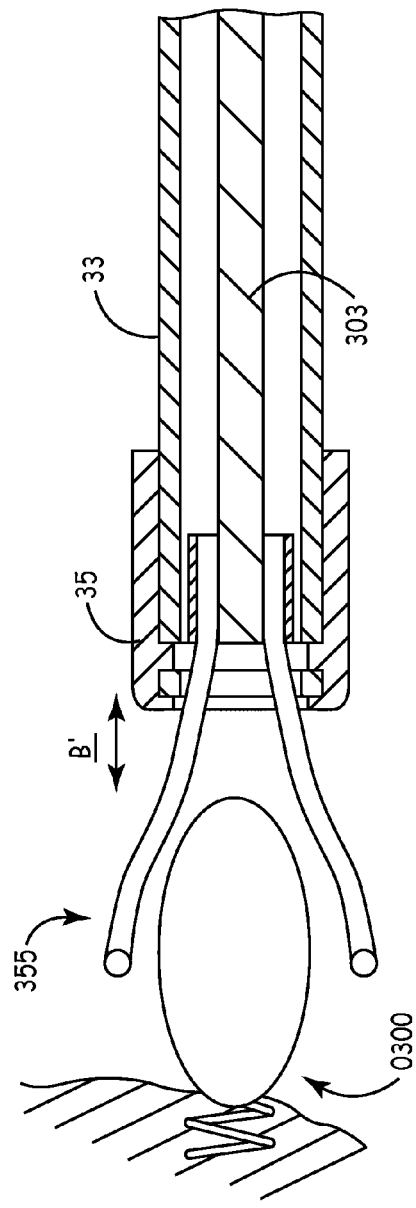
FIG. 3C is an enlarged plan view, including a cut-away section, of a portion of the tool shown in FIG. 3B.

FIG. 3C is an enlarged plan view, including a cut-away section, of a portion of tool 350, wherein grippers 255 have been pushed out from head 35 to release marker assembly O300 after assembly O300 has been implanted via rotation of grippers 355. FIG. 3C shows a cable 303 extending within shaft 33; cable 303 couples grippers 355 to portion 36 of handle 37 in order to drive the rotational and longitudinal movement of grippers. Commonly assigned U.S. Pat. No. 6,010,526 describes an implant tool similar to tool 350, which is incorporated herein by reference in it's entirety.

According to embodiment of the present invention, tool 350, gripping a marker, for example, marker assembly O300, may be passed through a subxyphoid or trans-thoracic port providing access to, for example, an endocardial surface of a heart wall. According to other embodiments of the present invention, tool 350 is passed through a guiding catheter, which provides transvenous access, for example, to an endocardial surface of a heart wall; the catheter may be steerable or just pre-formed according to embodiments well known to those skilled in the heart. With reference back to FIG. 3B, it may be appreciated that tool 350 may be constructed to be steerable such that handle 37 may manipulate portions of shaft 33, for example, via arrows C and/or D, to form bends, in order that a guiding catheter for tool 350 is not necessary; implementation of push and pull wires into shaft 33 may be accomplished according to methods known to those skilled in the art of steerable catheter construction. Referring back to FIG. 3A, an alternate fixation method may be facilitated by an optional slot 39 formed in body 304. According to the alternate method, a head of a driver tool, for example, very similar to a screw driver head, can be mated with slot 39 to both push marker assembly O300 against an implant site and to rotate the assembly to cause helix 345 to screw into the site thereby affixing the assembly to the site. The driver tool and assembly O300 may be delivered either through a cannula providing port access to an epicardial surface of a heart, or via a guiding catheter providing transvenous access to an endocardial surface of a heart, in a manner similar to that previously described for tool 350.

Figure 3D:
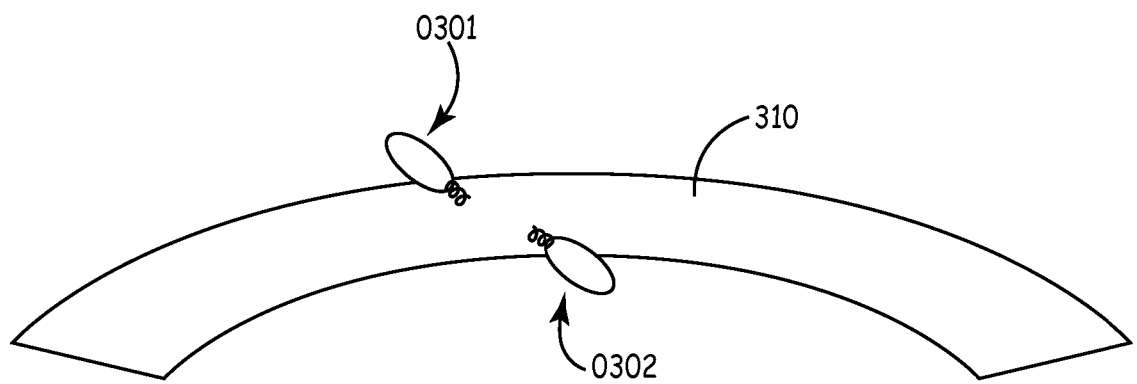
FIG. 3D is a schematic depiction of implanted markers, according to some embodiments of the present invention.
Figure 3E:
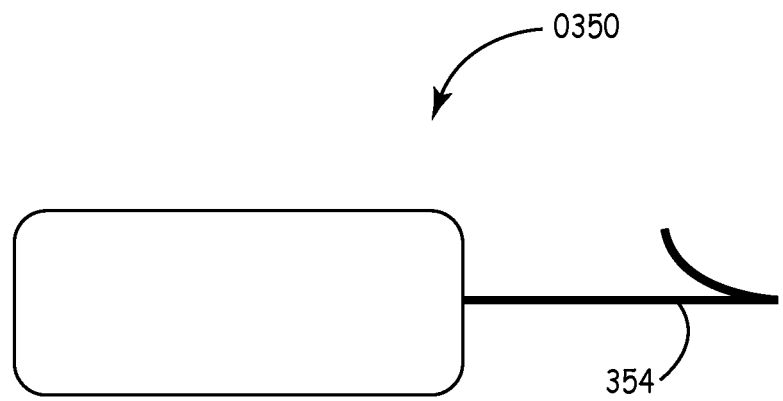
FIG. 3E is a plan view of an alternate embodiment of an implantable marker.

According to some alternate embodiments, independent markers O need not include a fixation element, like helix 345 or a barbed element 354 (FIG. 3E). For example, if an independent marker O, without a fixation element, is injected into heart tissue by a needle-type tool, the embedment or encapsulation of the marker may be sufficient to keep the marker fixed in place. According to another example, if independent marker O, without a fixation element, is implanted on an epicardial surface of the heart, the pericardium surrounding the heart and subsequent scar tissue may provide sufficient force to keep the marker fixed in place.

FIG. 3D is a schematic depiction of implanted independent markers O, according to some embodiments of the present invention. FIG. 3D illustrates a first independent marker O301 implanted, via helix fixation, adjacent to an epicardial surface of a portion of a heart wall 310 and a second independent marker O302 implanted, via helix fixation, adjacent an endocardial surface of the portion of heart wall 310. According to the illustrated embodiment, markers O301,302 can be interrogated, via excitation and collection of the response therefrom, to gain positional information indicating a thickness of wall 310, which, like chamber volume, can be monitored both over a short term, for example, over a cardiac cycle or a successive series of cardiac cycles, and over a long term, for example, over a series of interrogations spaced apart in time, wherein wall thicknesses at specific points in the cardiac cycle, for example, end diastole, may be tracked. A normal heart may have an average left ventricular wall thickness of about 1 cm; this average wall thickness may increase to approximately 2 cm, for example, in the case of hypertrophy (associated with common cardiac disease states, such as systemic hypertension or diastolic dysfunction), and may decrease to approximately 0.5 cm, for example, in the case of ischemia or dilated cardiomyopathy. With further reference to FIG. 3D, it may be appreciated that markers O301,302 are attached to wall 310 via a helix extending therefrom, for example helix 345 of FIG. 3A, rather than being embedded in wall 310. FIG. 3E is a plan view of an alternate embodiment of an implantable marker O350 including barbed fixation element 354, which upon being pushed into wall 310, would attach marker O350 to wall 310, so that the maker is adjacent to the wall, rather than being embedded therein, as is illustrated for markers O301,302. Thus, if implantable markers have dimensions approaching an average thickness of wall 310, these types of marker fixation can accommodate a placement of the markers with a sufficient gap therebetween to allow an appropriate resolution of positional information collected from one marker with respect to that collected from the other marker, so that chronic changes in the average thickness of heart wall 310, for example, due to hypertrophy or ischemia, may be tracked via the markers.

Certain changes in cardiac wall thickness, over a cardiac cycle, may be correlated to malfunction of ventricular contraction and thereby interpreted to diagnose ischemia. Time varying wall thickness may be used to calculate regional strain (i.e. STRAIN=100%×[{END DIASTOLIC WALL THINCKNESS−END SYSTOLIC WALL THICKNESS}/END DIASTOLIC WALL THICKNESS]). Changes in the phasic morphology of the wall thickness signal, as indicated by regional strain, might decrease from about 15% to −5% due to ischemia—an indication of regional dyskinesis. According to some methods of the present invention, the wall thickness positional information obtained from markers O31,32 is used to calculate the regional strain thereby facilitating diagnoses of dyskinesis secondary to ischemia.

Alternately, a wall thickness signal, over a cardiac cycle, generated by markers O31, 32, along with a time derivative thereof, can be used in place of chamber dimension signals, for example, as will be described below in conjunction with FIGS. 7A and 7C-D. According to some embodiments of the present invention multiple pairs of markers O31,32 may be implanted at strategic locations along heart wall 301.

Figure 4A:
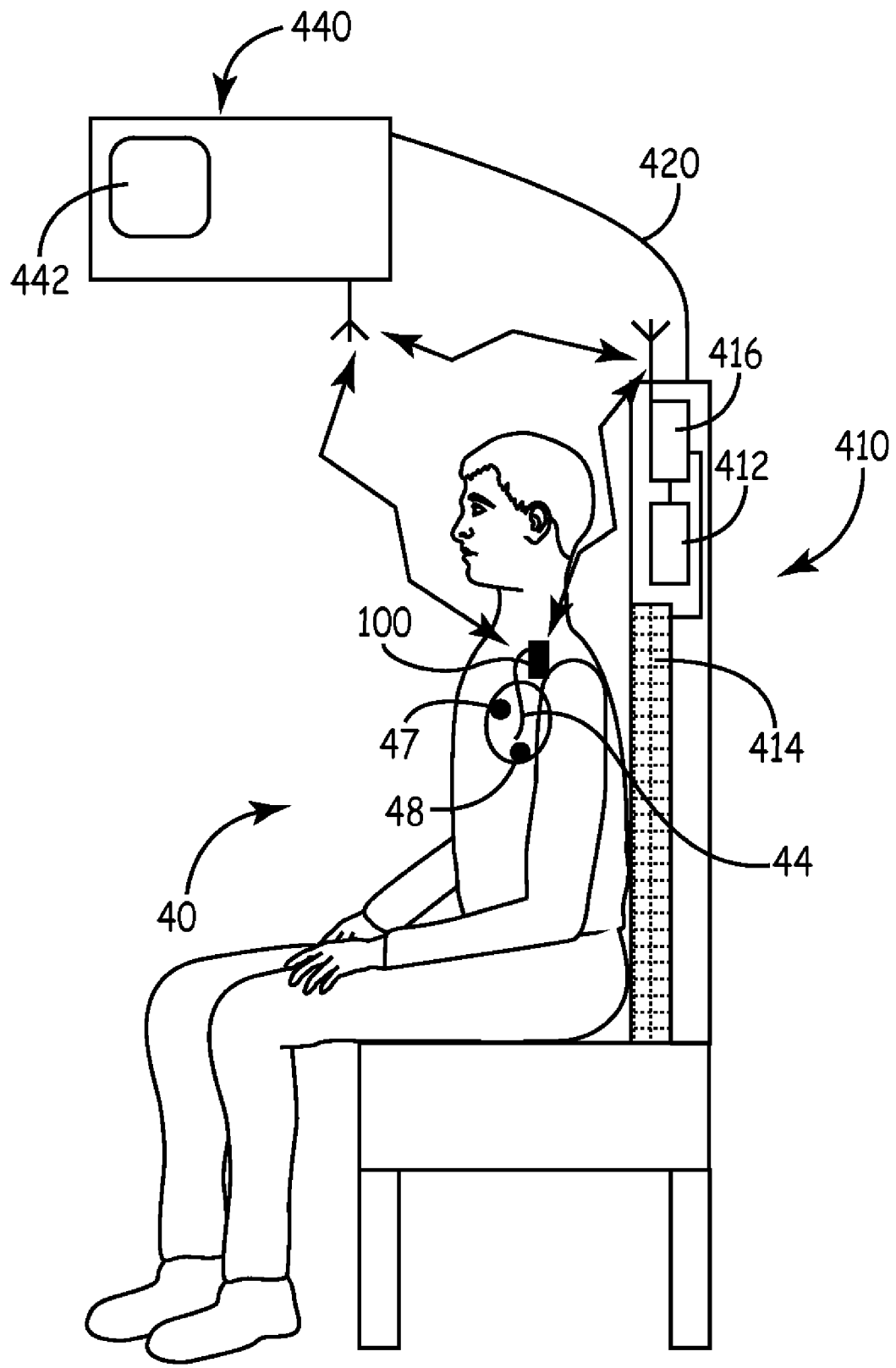
FIG. 4A is a schematic depiction of a system according to some embodiments of the present invention.

Turning now to FIG. 4A, external components facilitating interrogation of markers X, O will be addressed. FIG. 4A is a schematic depiction of a system, according to some embodiments of the present invention. FIG. 4A illustrates the system including IMD 100 implanted in a patient 40, an elongate member 44 extending from IMD into a heart of patient 40, independent markers 47, 48 (either X-type or O-type) implanted in/on the heart of patient 40, a marker interrogator 410, being built into a chair supporting patient 40, and an external analyzer 440. Analyzer 440 is shown coupled to interrogator 410, to collect positional information therefrom, via a cable 420 and telemetry, but may be coupled via only one or the other, according to some embodiments. According to some other embodiments, another external device (not shown), for example a home monitor, may collect the positional information from interrogator 410, either via a hard-wire connection or wirelessly, and then pass the information along to analyzer 440 at a remote location, via telemetry or a telephone line.

Figure 4B:
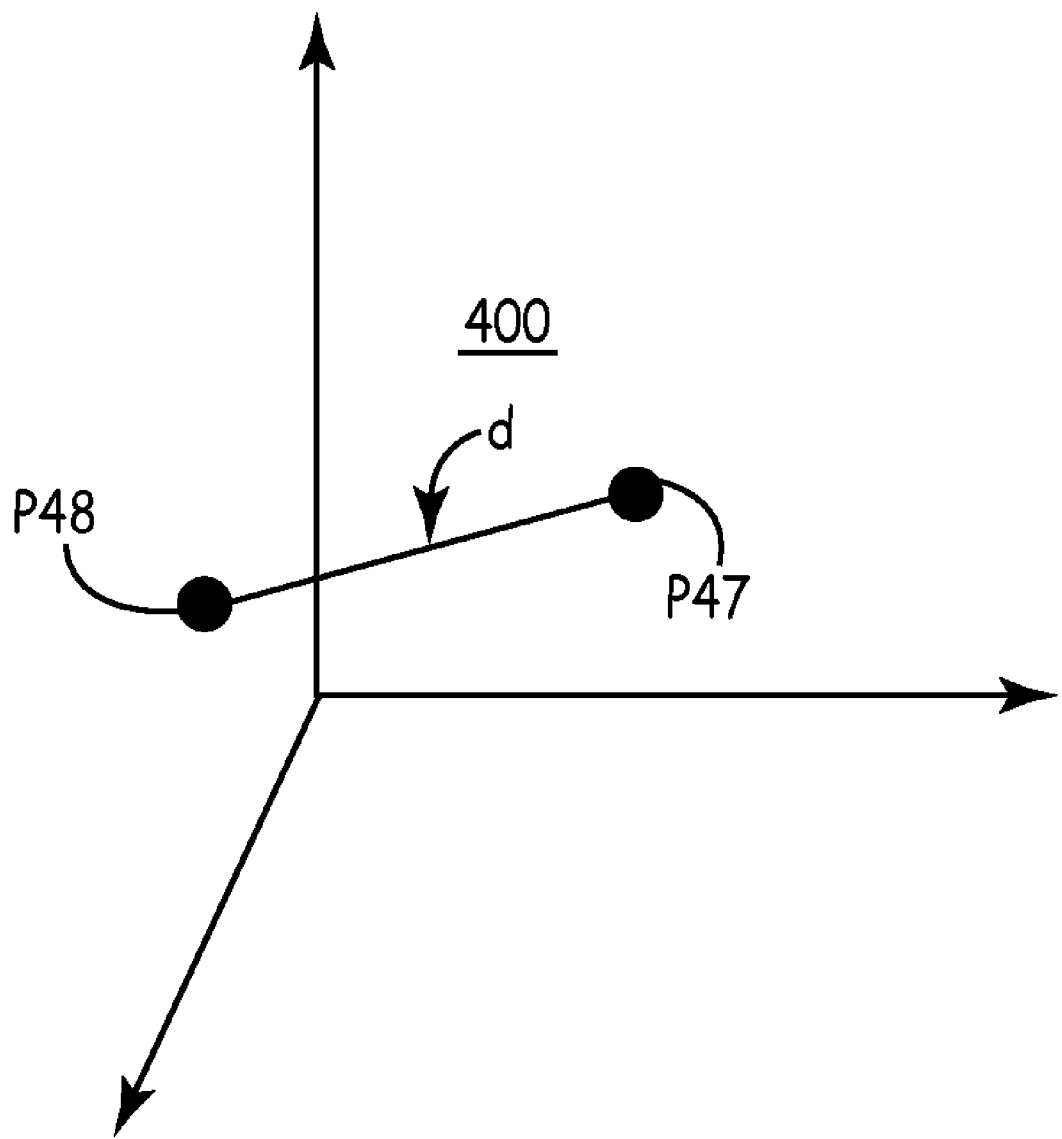
FIG. 4B is a schematic depiction of positional information, according to some embodiments of the present invention.

FIG. 4A further illustrates marker interrogator 410 including a pulsed source generator 412, for transmitting an excitation signal to markers 47, 48, a sensor array 414, for receiving a signal from each of markers 47, 48, in response to the excitation signal, and a marker signal processor 416, for converting the received response signals into positional information for each of markers 47, 48, the positional information, for example, defining an absolute real time distance between markers 47, 48. According to an exemplary embodiment, source generator 412 generates a selected electromagnetic excitation field or excitation signal that energizes markers 47, 48 so that each of the markers generates a measurable response signal to be picked up and measured by sensor array 414 for processing by processor 416, which uses the measurements of array 414 to calculate a location of each marker in three-dimensional space with respect to a fixed frame of reference, for example, defined by the structure of interrogator 410 that holds, or supports, patient 40 in fixed relation to array 414. Interrogator 410 may be constructed according to the teachings of U.S. Pat. No. 6,822,570, which is incorporated herein by reference in it's entirety. Interrogator 410 may be built into other structures, examples of which include, without limitation, a bed, a bathtub, a treadmill, or even a device implanted within patient 40. With reference to FIG. 4B, once a location P47, P48 of each marker 47, 48, in a frame of reference 400, is established by processor 416, processor 416 may calculate positional information for markers 47, 48 as a distance d. (It should be noted that the inventors also contemplate incorporation of markers which are self-excited, being battery operated; these markers could periodically transmit unique identification signals, which contain positional information, to a signal receiver.)

Figure 5:
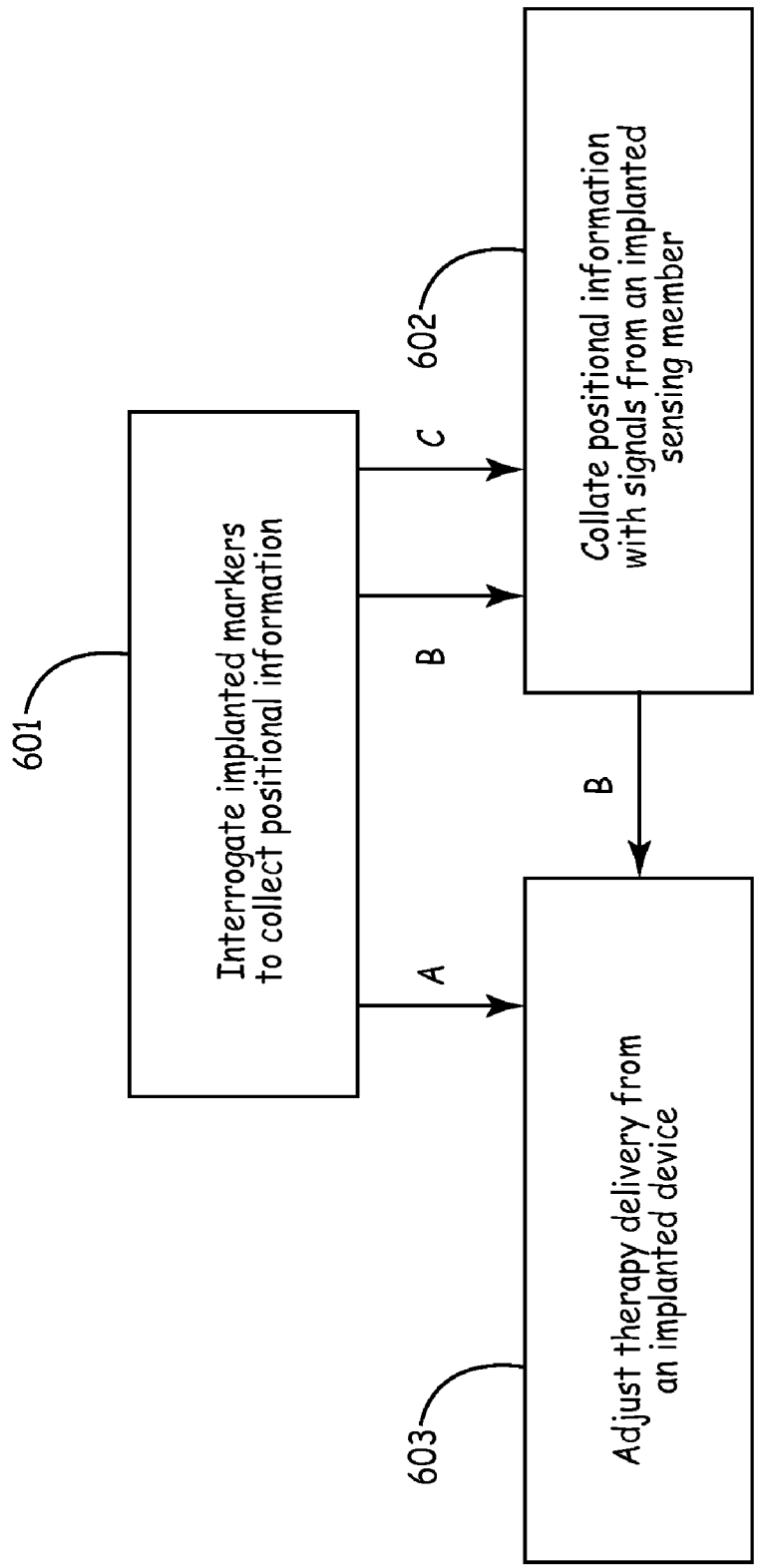
FIG. 5 is a flow chart outlining some methods of the present invention.
Figure 6:
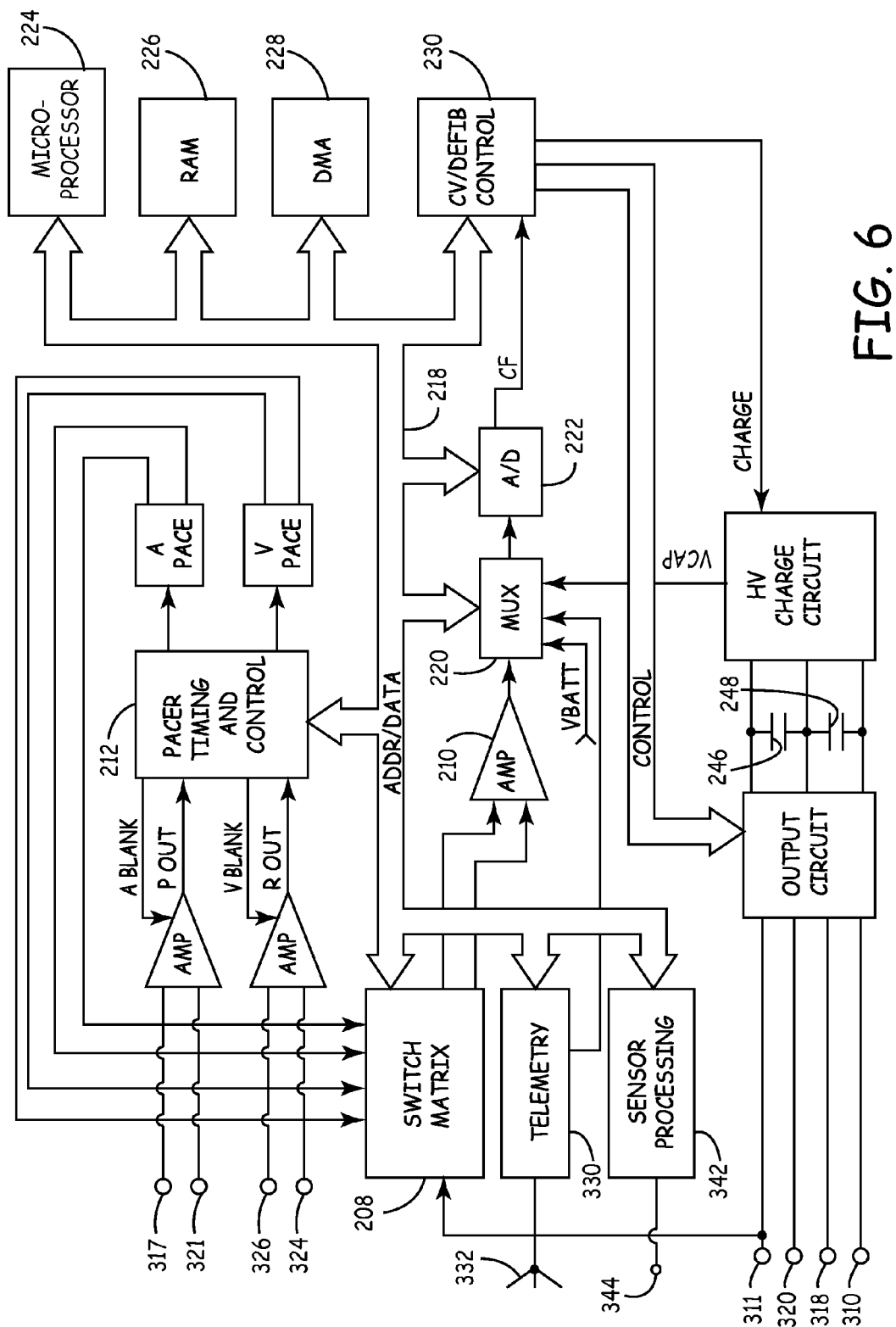
FIG. 6 is a functional block diagram for an exemplary implantable medical device included in a system, according to some embodiments of the present invention.

According to some embodiments of the present invention, to facilitate a medical diagnosis, external analyzer 440 combines or collates the positional information, received for each of markers 47, 48, with signals received from a sensing member coupled to elongate member 44, the signals having been transmitted from IMD 100, for example, via a telemetry circuit 330 and antenna 332 of IMD 100 as illustrated in FIG. 6. The sensing member may be one or more electrodes, for example electrodes 141, 143 shown in FIG. 1 for recording electrocardiograms, or a hemodynamic sensor, for example, pressure transducer 144, also shown in FIG. 1, or any other type of sensor known to those skilled in the art (e.g. impedance sensor, blood oxygen saturation or pH sensor, or accelerometer). It should be noted that the sensing member need not be coupled to IMD 100 via elongate member 44, in which case, member 44 is not an essential component of the illustrated system. FIG. 4 shows external analyzer 440 including a monitor 442 on which charts/plots of the combination of sensor signals and positional information may be displayed; analyzer 440 may further generate a printed report via a printer (not shown) coupled thereto. With reference to FIG. 5, which is a flow chart outlining some methods of the present invention, steps 601 and 602, via a pathway C, generally describe a method facilitating medical diagnoses which may be performed by these embodiments.

According to additional embodiments, elongate member 44 is adapted solely for therapy delivery from IMD 100, for example, via delivery of some therapeutic agent through a lumen thereof or via electrical stimulation by one or more electrodes thereof. Therapy delivery from IMD 100 may be defined and/or adjusted according to pre-programmed instructions in combination with the positional information, transmitted from marker interrogator 410, either directly, or through external analyzer 440, via telemetry, to a controller of IMD 100, for example, incorporated in a microprocessor 224 of IMD 100 wherein the instructions are programmed (FIG. 6). FIG. 5 outlines such a method for therapy delivery by steps 601 and 603, via a pathway A. Examples of therapy delivery include, without limitation, electrical stimulation and drug therapy. With respect to electrical stimulation, adjustment of the therapy may be accomplished by one or both of: altering pacing parameters within IMD 100, and repositioning one or more electrodes coupled to member 44 in order to find a pacing site at which pacing stimulation can elicit a better hemodynamic response. It should be noted, that, according to alternate embodiments, the therapy is delivered by means other than through IMD 100, for example, from another implanted device like a drug pump or from a source external to patient 40.

If the illustrated system further includes an implanted sensing member, therapy delivery from IMD 100 may be defined and/or adjusted according to a combination or collation of sensor signals with the positional information, for example, as outlined in FIG. 5 by steps 601, 602 and 603 via a pathway B. According to exemplary embodiments, the sensing member is a pressure transducer, one embodiment of which may be constructed according to the teaching of commonly assigned U.S. Pat. No. 6,221,024, which incorporated herein by reference in it's entirety.

FIG. 6 is an exemplary functional block diagram for an embodiment of IMD 100 that is adapted to receive and analyze electrical cardiac signals along with other signals transmitted by a sensing member or sensor (e.g. a pressure transducer, a blood oxygen saturation or pH sensor, an accelerometer, or any other type of sensor known to those skilled in the art), and to provide electrical stimulation therapy in the form of cardiac pacing and defibrillation. According to the illustrated embodiment, terminals 317 and 321 electrically connect atrial electrodes, for example, as would be coupled to lead body 12 shown in FIG. 1, to an atrial sense amplifier 204, and terminals 324 and 326 electrically connect ventricular electrodes, for example, electrodes 141 and 143 (FIG. 1), to a ventricular sense amplifier 200; each amplifier 204, 200 provides the appropriate atrial signal and ventricular signal, respectively to a pacer timing and control circuit 212 according to respective preset thresholds. Each of terminals 310, 311, 318 and 320 is shown coupled to a high voltage output circuit 234, wherein terminal 310 may electrically connect a coronary sinus defibrillation electrode, for example, as would be coupled to lead 16 shown in FIG. 1, terminal 311 may electrically connect to a housing of IMD 100, and terminals 318 and 320 may electrically connection to right ventricular and superior vena cava defibrillation electrode coils, for example, as would be coupled to lead 14 (FIG. 1). FIG. 6 further illustrates a terminal 344 for electrically connecting the sensing member to sensor processing circuitry 342, which is coupled to microprocessor 224 via a data/address bus 218, for the transmission of sensor signals.

With further reference to FIG. 6, a switch matrix 208, under control of microprocessor 224, is used to select, via bus 218, the electrodes which are to be coupled to a wide band amplifier 210 for use in digital signal analysis; the signals from the selected electrodes are directed through a multiplexer 220 and thereafter converted by an A/D converter 222 for storage in random access memory (RAM) 226, which is under the control of a direct memory access (DMA) circuit 228. Microprocessor 224 includes an associated ROM for storing programs that allow microprocessor 224 to analyze signals, transmitted thereto via bus 218, and to control the delivery of the appropriate therapy, for example, via pacing timing and control circuitry 212 and/or via cardioversion and defibrillation control circuitry 230 which initiates charging of high voltage capacitors 246, 248. Standard operation of the components shown in FIG. 5, which facilitate various sensing, pacing, cardioversion and defibrillation functions in conjunction with methods of the present invention, are well known to those skilled in the art.

Figure 7A:
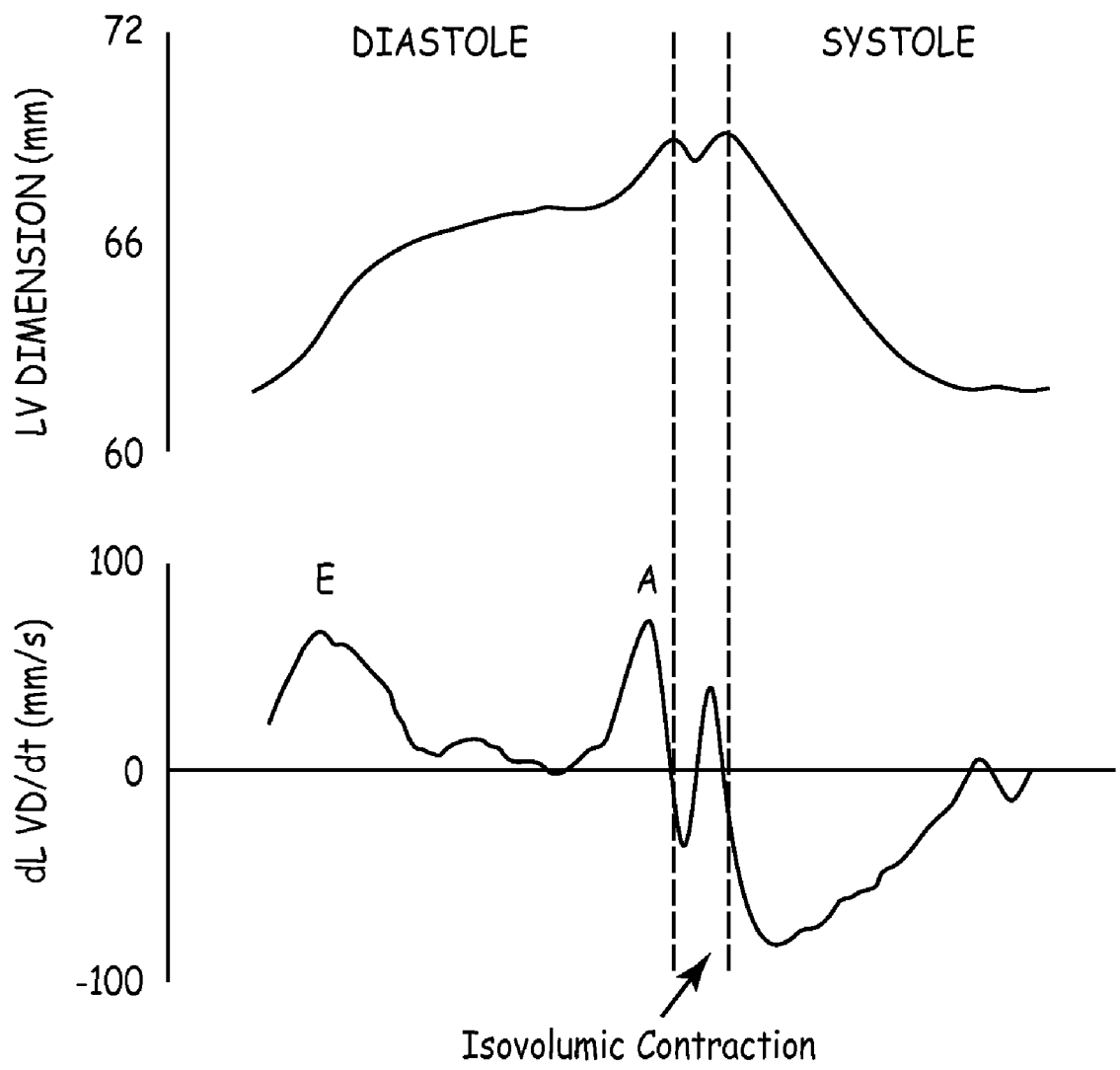
FIGS. 7A, 8A, 9A, 10 and 11 are various exemplary plots incorporating positional information from various systems of the present invention, each plot being useful for facilitating a medical diagnosis.

FIG. 7A shows related exemplary plots of LV dimension over a cardiac cycle. According to some embodiments of the present invention, at least two markers, for example, markers 47, 48 (FIG. 4), may be implanted on portions of an LV wall to provide positional information that may be converted to an LV chamber dimension, such as segment length or diameter, for example, as illustrated in the upper plot FIG. 7A, which is proportional to LV chamber size or volume. Such an LV dimension signal may be used, for example, to acutely or chronically monitor LV systolic and diastolic function, preload and synchrony of contraction. Some examples of cardiac indices that may be determined via an LV dimension signal include, without limitation, end diastolic dimension, percent dimensional shortening (i.e. strain), stroke volume, premature shortening and isovolumic lengthening. FIG. 7A also shows a plot of the derivative of the LV dimension signal, which is proportional to mitral valve flow during LV filling (diastole) and aortic valve flow during LV ejection (systole); points on the plot denoted "E" and "A" have been shown to provide useful information about LV filling that can be used to control pacing from device 100. For reference, FIGS. 7C-D are exemplary Echo Doppler plots, showing mitral valve flow and aortic flow, respectively. As previously mentioned, in conjunction with FIG. 3D, a wall thickness signal, along with a time derivative thereof, can be used in place of chamber dimension signals. Acute changes in wall thickness during the cardiac cycle are generally known to be inversely proportional to chamber volume. The time derivative of myocardial wall thickness is known to be generally inversely proportional to mitral valve flow during diastole and directly proportional to aortic flow during systole.

As an alternative to monitoring a changing chamber dimension over each cycle in a successive series of cardiac cycles, the positional information can be collected from markers at a particular point within successive cycles, provided that cardiac rhythm is consistent over the period of measurement. Signals from an implanted sensing member may be used to trigger interrogation of markers; for example, interrogation starting just prior to the point of LV isovolumic contraction can be triggered by a ventricular depolarization sensed from electrodes 141 and 143.

Figure 7B:
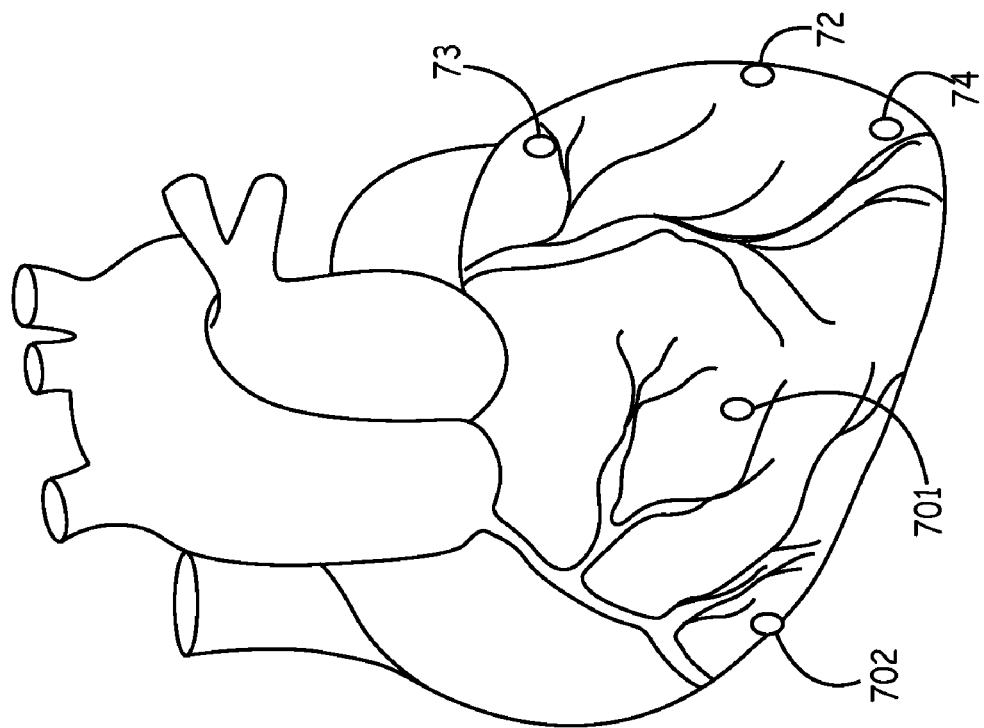
FIGS. 7B, 8B and 9B are schematics of a heart showing various locations of markers according to alternate embodiments of the present invention.
Figure 7B:
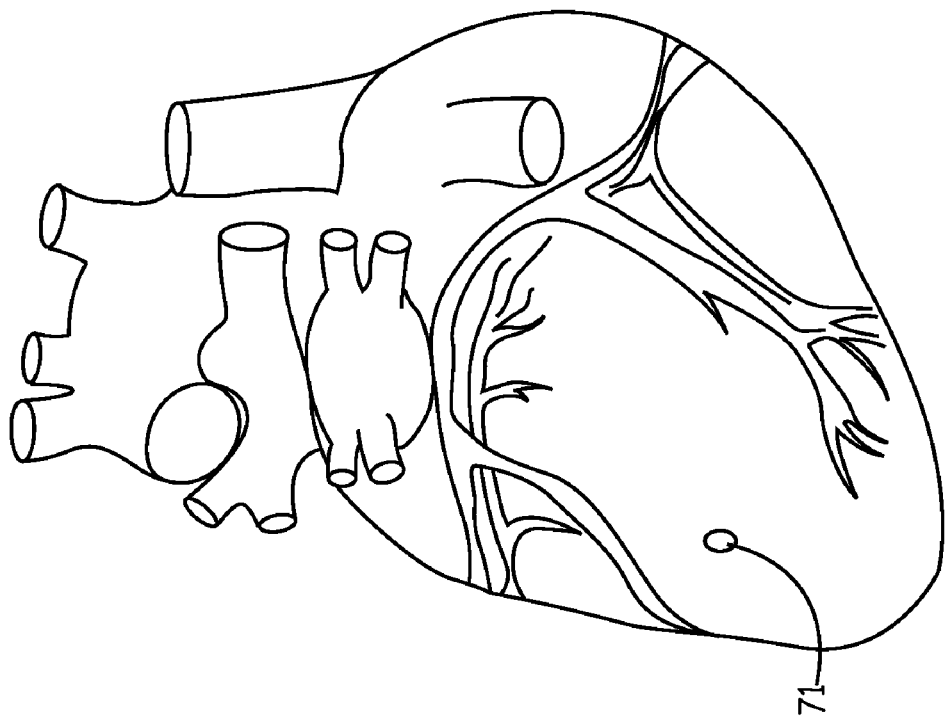
Figure 7C:
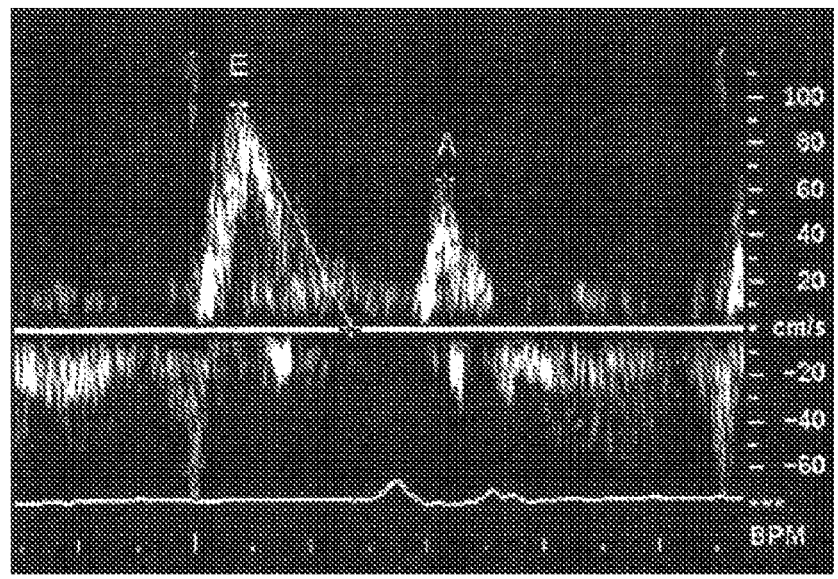
FIGS. 7C-D are exemplary Echo Doppler plots.
Figure 7D:
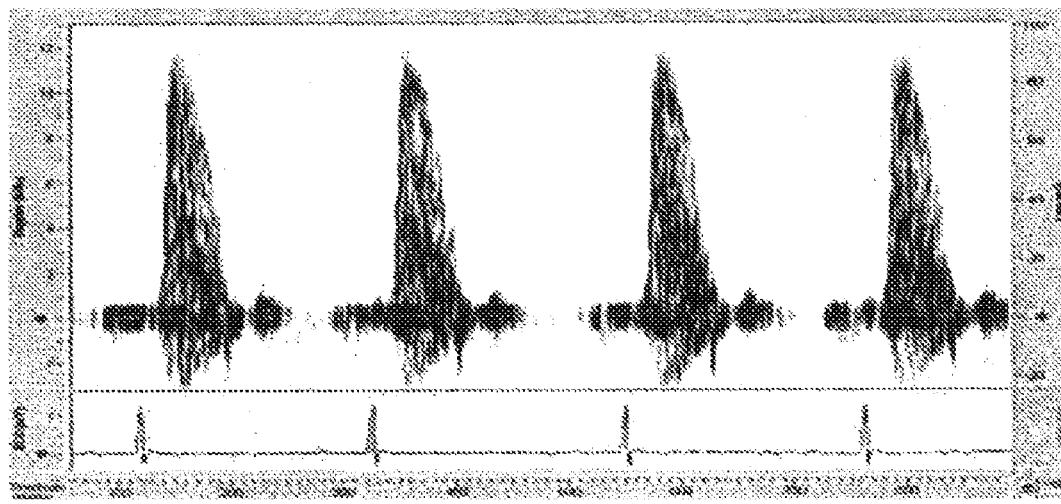

Exemplary locations for pairs of markers, from which positional information may be collected, for example, to generate the plots of FIG. 7A, according to some embodiments of the present invention, are shown in FIG. 7B. FIG. 7B is a schematic of a heart showing posterior and anterior views thereof. FIG. 7B illustrates markers 71 and 72 located for tracking of a dimension of a left ventricle along a short axis thereof; markers 73 and 74 located for tracking of another dimension of the left ventricle along a long axis thereof. FIG. 7B further illustrates another pair of markers 71 and 701 located to track a dimension of both the left ventricle and a right ventricle along a short axis thereof; and yet another pair of markers 701 and 702 located to track a dimension of a segment of the right ventricle.

A pair of markers positioned on sides of a left atrium (LA) may likewise provide positional information that can be converted to LA segment length, diameter, or volume. LA volume is presented in a plot shown in FIG. 8A, wherein a peak, denoted "MVO", corresponds to the opening of the mitral valve and the start of LV filling, and a valley, denoted "MVC", corresponds to the closing of the mitral valve just after the end of LA systole. Tracking LA dimension, acutely or chronically, may be useful in detecting remodeling of the LA, in discriminating between atrial fibrillation and atrial flutter, in detecting atrial arrhythmias, and in detecting venous or pulmonary congestion.

Figure 8A:
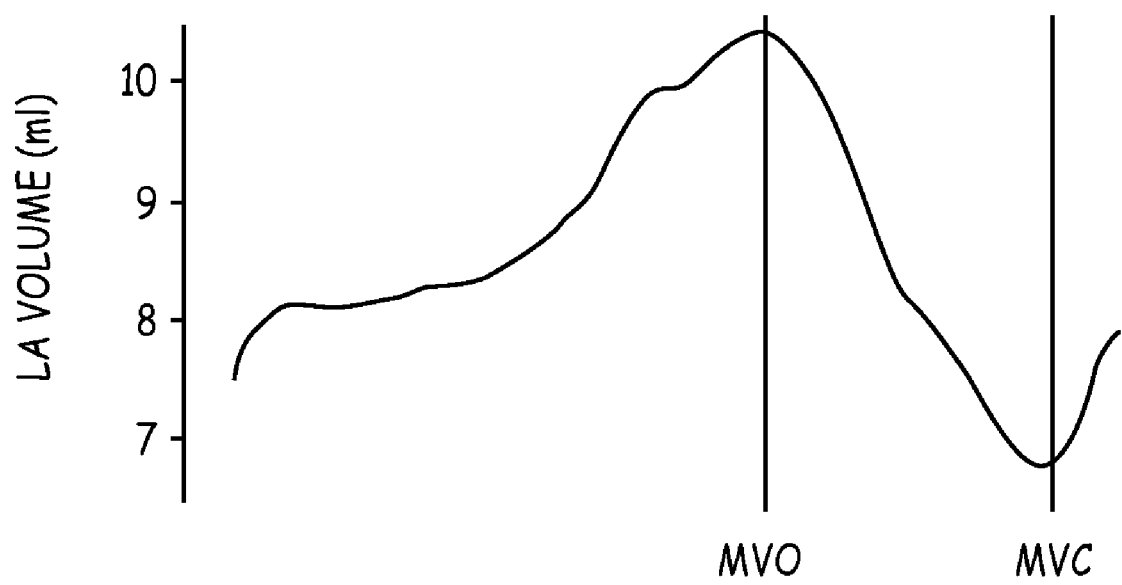
Figure 8B:
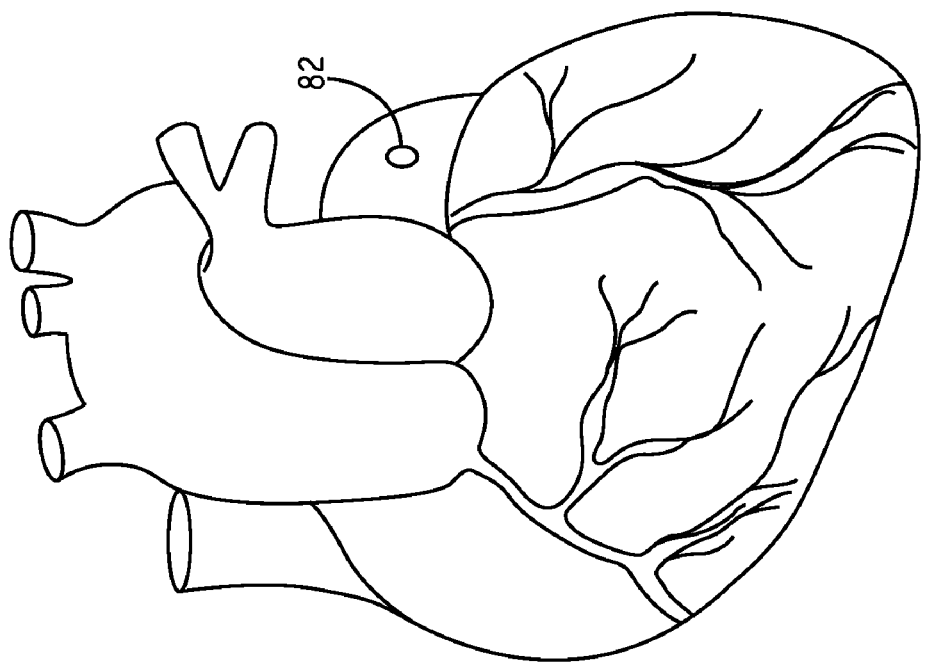
Figure 8B:
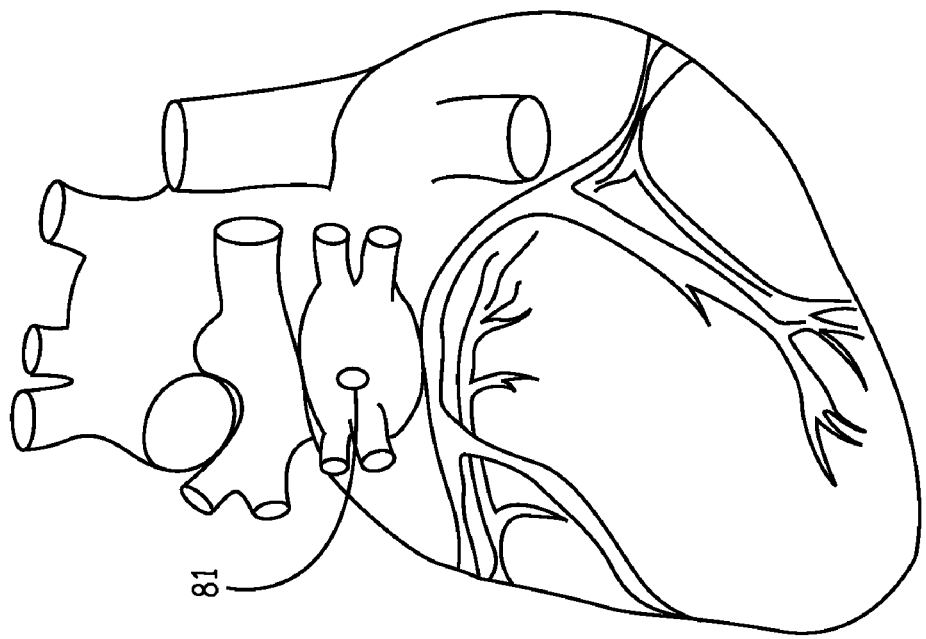

An exemplary location for a pair of markers 81 and 82, from which positional information may be collected, for example to generate the plot shown in FIG. 8A, according to some embodiments of the present invention, are shown in FIG. 8B. FIG. 8B is a schematic of a heart showing posterior and anterior views thereof. FIG. 8B illustrates marker 81 disposed on a posterior side of a left atrium and marker 82 disposed on an anterior side of the right atrium.

A pair of markers positioned on opposing sides of any of the great vessels, for example, aorta, pulmonary artery, pulmonary veins, or either vena cava, can provide positional information indicating changing dimensions of the vessel over the cardiac cycle, which can be used to monitor, for example, ventricular afterload, arterial compliance, aortic distensibility, venous reserve, and venous tone (i.e. compliance). Positional information indicating atrial, ventricular or venous dimension can be collected in order to monitor pulmonary or peripheral edema. For example, a gradual and sustained increase in left atrial or pulmonary venous size might be associated with pulmonary congestion.

Figure 9A:
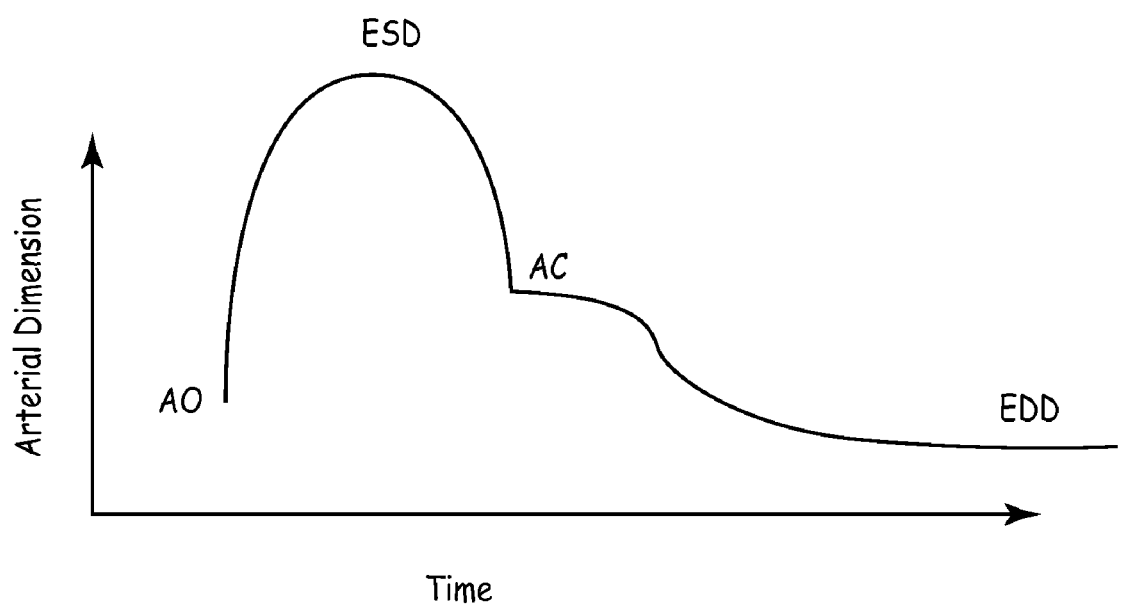

FIG. 9A shows an exemplary plot of arterial dimension over a cardiac cycle (the shape corresponding to an arterial pressure signal), which can be generated from positional information garnered from markers attached to opposing walls of an aorta. The exemplary plot indicates a stretching of the aorta in response to LV ejection (systole), that starts when the aortic valve opens (AO), an end-systolic dimension (ESD), and an end-diastolic dimension (EDD), following aortic valve closure (AC). Such a plot generated over successive cycles can provide information concerning changing LV afterload (related to the strain imparted to the aorta, calculated from ESD and EDD, which is indicative of arterial compliance). Such information can be used in determining when and how to adjust cardiac therapy, for example, delivered from IMD 100. Afterload is commonly defined as the forces opposing ventricular ejection; two components of ventricular afterload are total peripheral resistance (primarily a result of arteriolar vessel tone) and total arterial compliance (primarily a property of the aorta). Changes in LV afterload are commonly known to change LV relaxation patterns, and thus impact LV filling (Solomon S B, Nikolic S D, Frater R W, Yellin E L. Contraction-relaxation coupling: determination of the onset of diastole. Am J. Physiol. 1999 July; 277(1 Pt 2):H23-7). Therefore, adjusting those programmable parameters of IMD 100, which control cardiac therapy and affect arterial pressure or dimension, for example, lower rate, AV delay, pacing mode or pacing location, can lead to improved LV filling. For example, Solomon et al. indicate that LV afterload is frequency dependent, being lower at certain frequencies. Therefore, a pacemaker could optimize heart rate according to the information concerning afterload (determined, in whole or part, from aortic dimension), to minimize LV afterload.

Figure 9B:
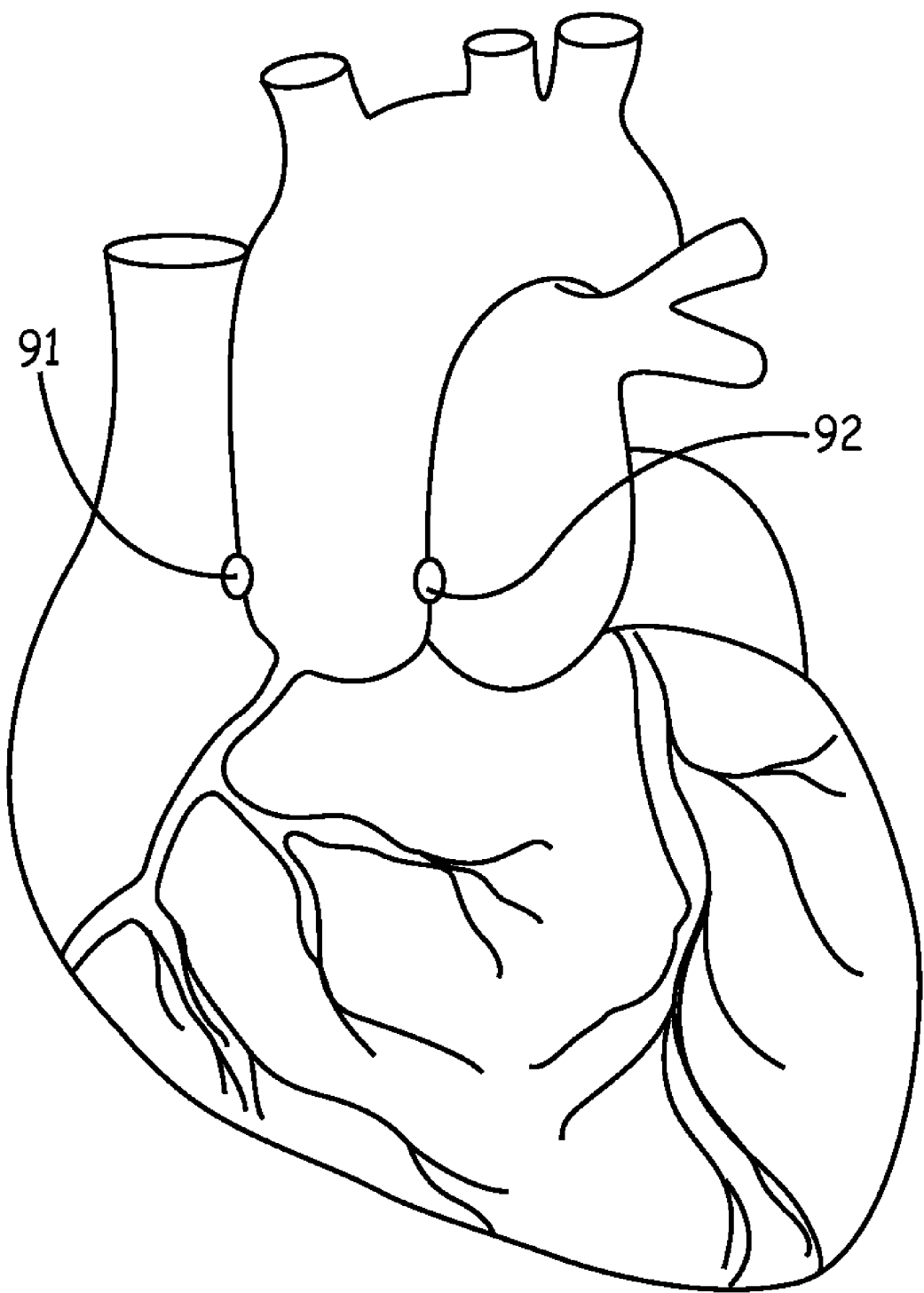

FIG. 9B is an anterior view of a heart showing an exemplary location for a pair of markers 91 and 92, from which positional information may be collected to generate the plot of FIG. 9A, according to some embodiments of the present invention. FIG. 9B illustrates markers disposed on opposing walls at a root of an aorta.

Figure 10:
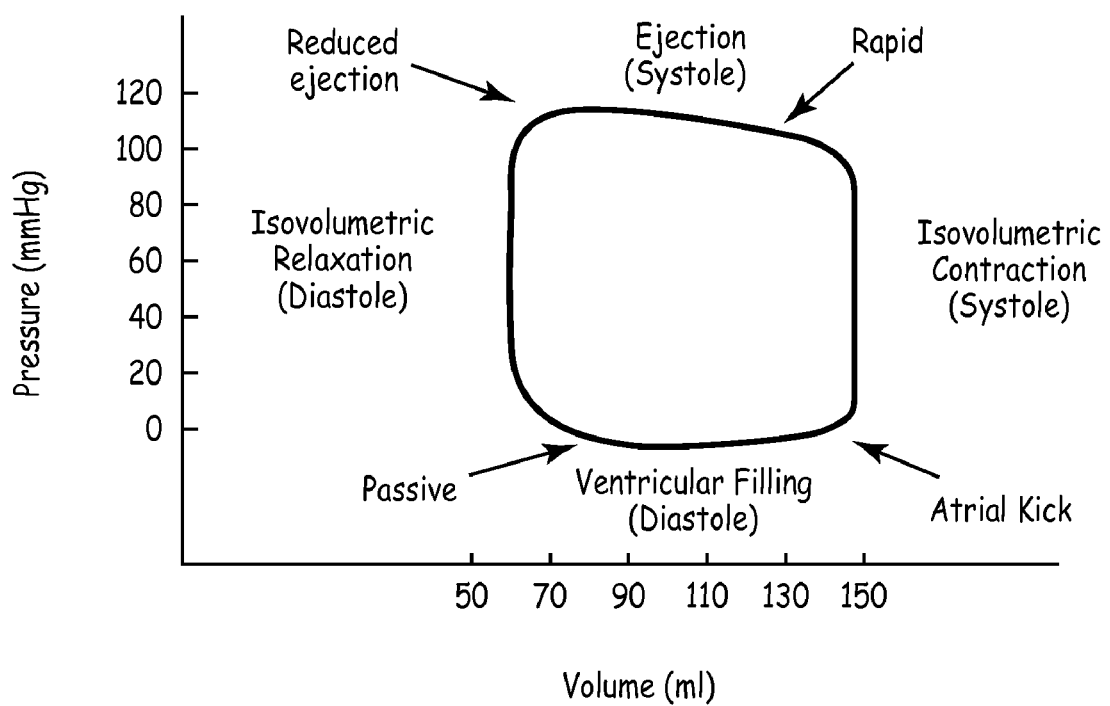

Positional information corresponding to any of the above chambers or vessels may be combined with signals from an implanted sensing member, as previously described. Alternately, changes in any of the aforementioned dimensions can be used to estimate pressure within a chamber or great vessel, if an estimate of chamber compliance were available, since dimensional changes, in general, follow changes in pressure. According to some embodiments of the present invention, a pressure measured within a chamber, for example, aorta, RV, LV or LA, is collated with positional information from markers implanted on or in the chamber. According to an exemplary embodiment, a pressure transducer sensing member is positioned in the RV (preferably in close proximity to the outflow tract of the RV), for example transducer 144 shown in FIG. 1, and a pair of markers are coupled to a wall of the RV, for example, markers 701, 702 shown coupled to the anterior free wall of the RV in FIG. 7B, in order to obtain pressure and positional information, which may be combined to generate an RV pressure dimension phase plot or 'loop' for an individual cardiac cycle, for example, as displayed in FIG. 10. Several well known indices of ventricular function (i.e. stroke work), afterload (i.e. effective arterial elastance), preload (i.e. end diastolic dimension), diastolic function (i.e. myocardial stiffness), viscosity, systolic function (i.e. end systolic elastance), preload recruitable stroke work, etc., could be determined from such a display. Each of these indices could be used in a simple closed loop feedback system to control device programmable parameters including pacing rate, delay, site, and mode.

Figure 11:
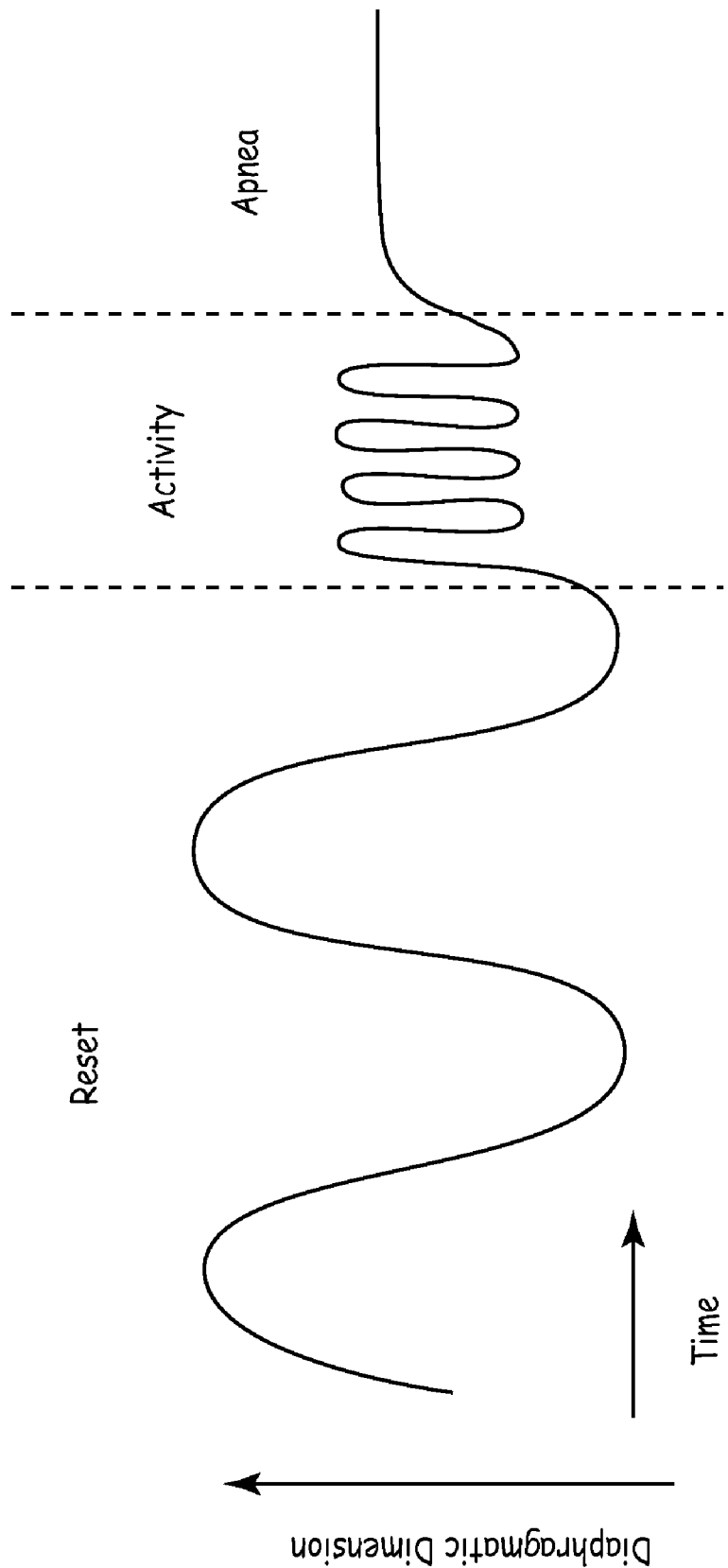

Referring back to FIG. 1, in combination with FIG. 11, markers may be attached to diaphragm 110 in order to provide positional information related to the expansion and contraction thereof associated with respiration. FIG. 11 shows a plot of a diaphragm dimension, for example, a distance between markers O attached to diaphragm 110 (FIG. 1), versus time, which is generally indicative of respiration rate under three conditions: at rest, during activity and during cessation of breathing, or apnea. Thus, the positional information from the diaphragm markers may be used to detect changes in breathing patterns which may warrant the commencement or adjustment of therapy delivery, for example, from IMD 100.

Positional information corresponding to any of the above applications may be used, either alone or in combination with signals from one or more implanted sensing members, to titrate a drug therapy, for example, inotropic or diuretic. For example, if a positive inotropic agent such as Dobutamine were to be infused for treatment of congestive heart failure, the changes in cardiovascular function, associated with the drug infusion, as determined via the positional information, can be used to optimize the prescribed dosage; likewise for the administration of a diuretic to address pulmonary congestion. Alternately, or additionally, an effectiveness of electrical stimulation therapy, for example pacing and/or defibrillation, may be assessed, via the positional information, and parameters defining the therapy delivery adjusted accordingly.

In the foregoing detailed description, the invention has been described with reference to specific embodiments. However, it may be appreciated that various modifications and changes can be made without departing from the scope of the invention as set forth in the appended claims.

The invention claimed is:

1. A system facilitating medical diagnosis, the system comprising:
    implantable markers to wirelessly transmit a signal in response to a wirelessly transmitted excitation signal, when the markers are implanted in a body;
    an excitation signal transmitter to transmit the excitation signal to the implanted markers;
    a marker signal receiver to receive the response signal from each of the two implanted markers;
    a marker signal processor to convert the received response signals into positional information, the positional information comprising a distance between the two markers;
    an implantable sensing member;
    an implantable sensing member signal processor adapted to receive signals from the sensing member, when the sensing member is implanted in the body;
    an analyzer to receive the positional information and the sensing member signals, and to collate the positional information with the sensing member signals;
    a positional information transmitter coupled to the marker signal processor and the analyzer; and
    an implantable sensing member signal transmitter coupled to the implantable sensing member signal processor and the analyzer.

2. The system of claim 1, wherein the sensing member signal transmitter includes at least one lead, and at least one marker of the two markers is coupled to a body of the lead.

3. The system of claim 1, wherein the sensing member is a pressure transducer.

4. The system of claim 1, wherein the sensing member is at least one electrode.

5. The system of claim 1, wherein the analyzer is a component of the implantable signal processor.

6. A medical therapy delivery system, comprising:
    implantable markers to wirelessly transmit a signal in response to a wirelessly transmitted excitation signal, when the markers are implanted in a body;
    an excitation signal transmitter adapted to transmit the excitation signal to the implanted markers;
    a marker signal receiver to receive the response signal from each of the two implanted markers;
    a marker signal processor to convert the received response signals into positional information, the positional information comprising a distance between the two markers;
    an implantable therapy delivery device including a controller to receive the positional information and to adjust a therapy delivered from the device according to the positional information;
    a positional information transmitter for transmitting the positional information to the device controller, the positional information transmitter coupled to the marker signal processor;
    an implantable sensing member; and
    a sensing member signal transmitter coupled to the device controller;
    wherein the device controller is further adapted to receive sensing member signals and to adjust therapy delivered from the device according to the sensing member signals in combination with the positional information.

7. The system of claim 6, wherein the sensing member is a pressure transducer.

8. The system of claim 6, wherein the sensing member is at least one electrode.

9. The system of claim 6, wherein the sensing member signal transmitter includes at least one lead and at least one marker of the two markers is coupled to a body of the lead.

10. A method of interrogating implanted markers for medical therapy delivery, comprising:
   wirelessly transmitting an excitation signal,
   wirelessly receiving a signal from each of the markers in response to the excitation signal,
   converting the response signal into positional information, the positional information comprising a distance between the two markers; and
   adjusting a therapy delivered from an implanted device according to the positional information;
   transmitting signals from an implanted sensing member to the implanted device; and
   wherein the therapy from the implanted device is adjusted according to the sensing member signals in combination with the positional information.

11. The method of claim 10, wherein adjusting the therapy comprises repositioning at least one pacing electrode coupled to the device.

12. The method of claim 10, wherein adjusting the therapy comprises altering pacing parameters within the device.

* * * * *